United States Patent
Devlin

(10) Patent No.: US 7,393,114 B2
(45) Date of Patent: Jul. 1, 2008

(54) LIGHTED GRIP AND ALLIGATOR CLIP CORD FOR TATTOO MACHINE

(76) Inventor: Joseph E. Devlin, 15865 River Birch Rd., Westfield, IN (US) 46074

( * ) Notice: Subject to any disclaimer, the term of this patent is extended or adjusted under 35 U.S.C. 154(b) by 684 days.

(21) Appl. No.: 10/936,958

(22) Filed: Sep. 9, 2004

(65) Prior Publication Data

US 2005/0090851 A1  Apr. 28, 2005

Related U.S. Application Data

(60) Provisional application No. 60/501,463, filed on Sep. 9, 2003, provisional application No. 60/506,969, filed on Sep. 29, 2003.

(51) Int. Cl.
| | |
|---|---|
| *F21V 33/00* | (2006.01) |
| *B43K 29/10* | (2006.01) |
| *B43K 5/00* | (2006.01) |
| *B25B 23/18* | (2006.01) |
| *A61B 17/34* | (2006.01) |
| *A61B 17/20* | (2006.01) |

(52) U.S. Cl. .................. 362/109; 362/118; 362/119; 362/120; 606/185; 606/186; 81/9.22; 604/47

(58) Field of Classification Search ............... 362/109, 362/118–120; 81/9.22; 606/116, 186, 185; 30/362; 604/47

See application file for complete search history.

(56) References Cited

U.S. PATENT DOCUMENTS

| | | | | |
|---|---|---|---|---|
| 3,919,541 | A * | 11/1975 | Chao | 362/120 |
| 4,228,485 | A * | 10/1980 | Hubbard et al. | 362/191 |
| 5,270,638 | A * | 12/1993 | Mellott | 324/133 |
| 5,376,076 | A * | 12/1994 | Kaali | 604/164.08 |
| 6,622,733 | B2 * | 9/2003 | Saksa | 132/200 |
| 2007/0053180 | A1 * | 3/2007 | Jones et al. | 362/118 |
| 2007/0076409 | A1 * | 4/2007 | Boesch et al. | 362/109 |

FOREIGN PATENT DOCUMENTS

DE  19818940 A1 * 11/1999

* cited by examiner

*Primary Examiner*—Jong-Suk (James) Lee
*Assistant Examiner*—David J Makiya
(74) *Attorney, Agent, or Firm*—Woodard, Emhardt, Moriarty, McNett & Henry LLP

(57) ABSTRACT

An assembly according to the present invention includes a tattoo machine, a grip attached to the tattoo machine, and a light assembly inside the grip utilizing light emitting diodes (LEDs). The assembly further includes a power supply, a power cord for connecting the tattoo machine to the power supply, and two alligator clips conductively connected to the power cord or tattoo machine which transmit power to the light assembly via wires extending from the light assembly to the alligator clips.

15 Claims, 7 Drawing Sheets

LIGHTED GRIP AND ALLIGATOR CLIP CORD FOR TATTOO MACHINE

CROSS REFERENCE TO RELATED APPLICATIONS

This application is based on provisional patent application Ser. No. 60/501,463, filed Sep. 9, 2003, and 60/506,969, filed Sep. 29, 2003, and priority is claimed based on all of these applications.

FIELD OF THE INVENTION

The present invention relates generally to tattooing and/or medical or dental procedures, and, more particularly, to a lighted grip device for lighting the surface of the skin, as well as a device to provide a power connection to accessories, such as a lighted grip, used during the tattooing process and/or medical or dental surgery process.

BACKGROUND OF THE INVENTION

Many present day tattoos involve small, intricate designs. Additionally, medical and dental procedures are often performed on small areas on the body. Operators presently rely on lighting sources, such as adjustable lamps, that often are large, awkward to move, require constant adjustment, and thus do not provide the optimal amount of light in the necessary locations, as is desired and necessary. Such a lighting source, because of its proximity to the subject, can cast shadows over the area where an operator is working which can adversely affect the operator's performance.

Additionally, in most cases this type of lighting source is lit with a standard 60 to 120 watt light bulb to provide ample lighting. However, the operator is now subjecting himself to over-exposure to bright light bulbs in order to remove shadows in the area where a subject is being examined. Additionally, higher wattage bulbs create excessive heat to both the operator and to the subject.

In particular, tattoos are applied by perforating the skin of a subject in a predetermined pattern with a needle and introducing one or more colored pigments into the perforations. Modern tattooing is performed using a tattoo instrument or tattoo machine comprised of a needle holder to hold the tattooing needle, an electric motor or other means, e.g., a solenoid, to rapidly reciprocate the needle, a power cord connection point which connects the power cord to the tattoo machine, a power source, a needle grip tube housing, and in many cases an adjustable grip which mounts to the grip tube housing by means of adjustable set screws.

Many present day tattoo assemblies use simple "L" shaped clips and a tension spring, both on one end of a power cord, to make a conductive connection to the tattoo machine. This cord in turn connects to a power source or foot-peddle to manually determine the electric current flowing to the tattoo machine, and therefore adjust the rate of speed by which the needle moves. This cord is made up of a standard copper wire of varying gauges that can safely manage the electrical current.

Additionally, operators presently rely on their capability to perform in an efficient work area. Certain accessories that can be utilized by an operator during the tattooing process, by their very design, do not provide for a convenient form of connection to the power cord. This can adversely affect the ability of an operator to provide consistently efficient work for consumers. Additionally, this inefficient capability to connect to the power cord could affect the life cycle of those accessories, causing unnecessary wear and tear to the accessory.

Thus, there remains a need for a new and improved way to light the area in a way that is compact, reduces shadows, and does not generate excessive heat transferred to either the subject or the operator. Additionally, there remains a need for a new and improved way to operate and provide power to accessories during use by the operator that is both efficient and reduces unnecessary wear and tear on accessories.

SUMMARY OF THE INVENTION

In preferred embodiments, the present invention is concerned with a lighted grip assembly for a tattoo machine or other surgical tool. Preferably, alligator clips are conductively connected to a power cord transmitting power to the tattoo machine or other surgical tool, and the alligator clips provide power to an accessory, such as the lighted grip assembly.

A preferred apparatus according to one embodiment of the present invention comprises a grip for attachment to a tattoo machine, wherein the grip includes a light assembly.

An assembly according to another preferred embodiment of the present invention involves a first alligator clip and a second alligator clip, with the first and second alligator clips being conductively coupled to a tattoo assembly to provide power to a device.

A further preferred embodiment of the present invention involves a tattoo assembly comprising a tattoo machine, a power cord for connecting the tattoo machine to a power supply, a grip around a portion of the tattoo machine, and a light assembly within the grip for lighting a section of skin.

Another preferred embodiment of the present invention is a tattoo assembly including a tattoo machine for injecting ink into skin, a grip for attachment to the tattoo machine, and a light assembly inside the grip. The light assembly includes at least one light emitting diode (LED) and a circuit board. The tattoo assembly further includes a power supply, a power cord for connecting the tattoo machine to the power supply, a first alligator clip, and a second alligator clip. The first and second alligator clips are conductively connected to the power cord for supplying power to the light assembly through wires extending from the light assembly to the alligator clips. The tattoo assembly preferably includes a transparent end cap for attachment to the grip, covering the light assembly.

DESCRIPTION OF THE PREFERRED EMBODIMENT

For the purposes of promoting an understanding of the principles of the invention, reference will now be made to the embodiment illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention generally concerns a lighted grip assembly attached to a tattoo machine or other surgical tool for lighting a section of skin. In a preferred embodiment, alligator clips are conductively connected to a power cord providing power to the tattoo machine or other surgical tool, wherein the alligator clips transfer power from the power cord to the lighted grip assembly or other such accessory.

Figure 1:
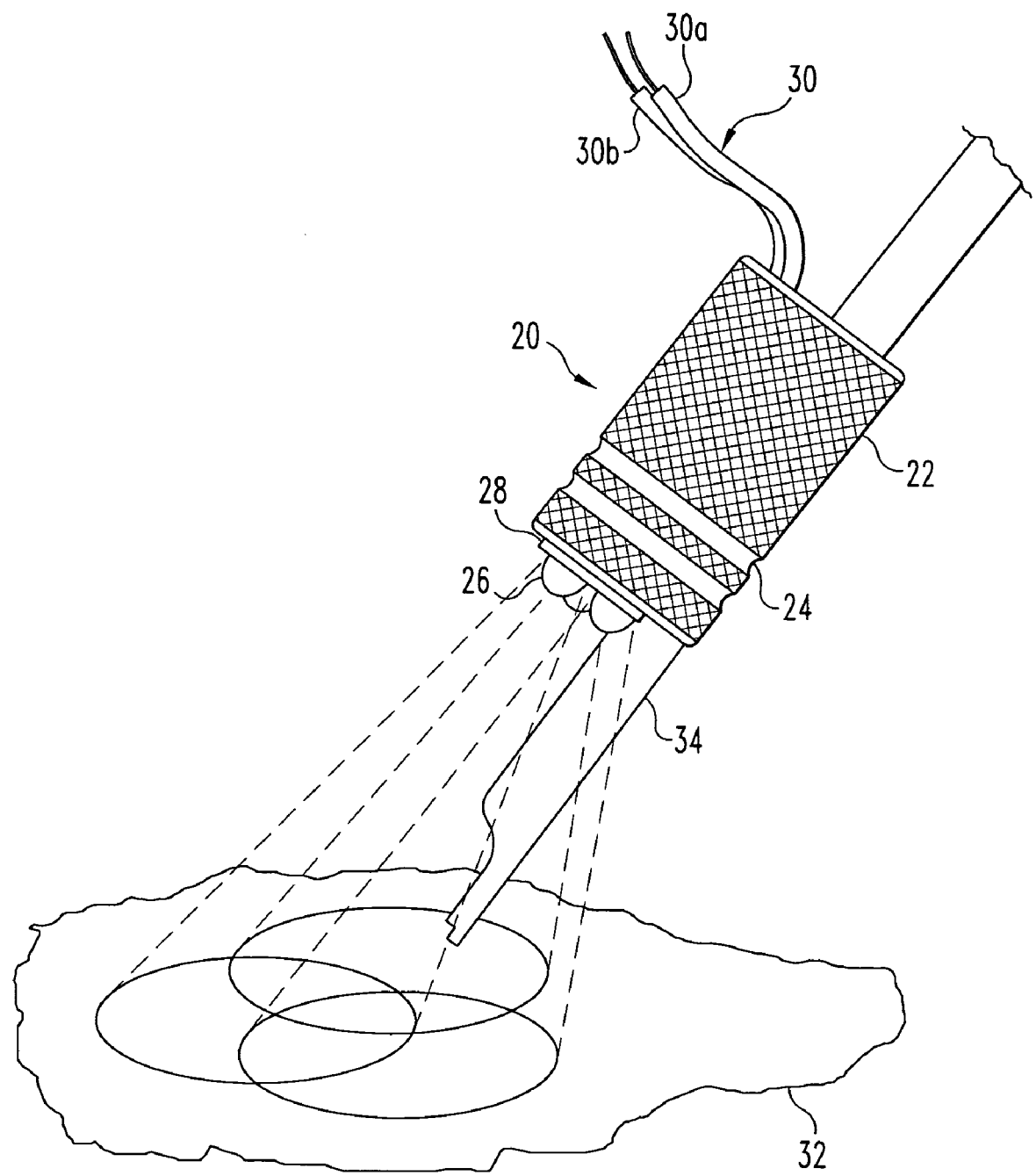
FIG. 1 is a perspective view of a lighted grip assembly on a tattoo machine.

FIG. 1 illustrates a lighted grip 20 according to one embodiment of the present invention. The lighted grip 20 includes a grip tube 22, grooves 24, light emitting diodes (LEDs) 26, a plate 28, and wires 30. The wires 30 include one positive power wire 30a and one negative power wire 30b. Additionally, the wires 30 are designed for connection to a power source to provide electric current to the lighted grip 20. The lighted grip 20 projects light onto a section of skin 32. The light produced by the lighted grip 20 reduces the need for other external light sources, reduces shadows created on the section of skin 32, and reduces eye strain of a user or operator of the lighted grip 20. The grooves 24 assist a user or operator in gripping and handling the lighted grip 20. In the illustrated embodiment, the lighted grip 20 is attached to a tattoo machine 34 designed to inject ink into the section of skin 32. However, it should be appreciated that the lighted grip 20 can be attached to any tool or device as would generally occur to one skilled in the art. In a preferred embodiment, the lighted grip 20 is cylindrically shaped; however, it should be appreciated that the lighted grip 20 can be shaped differently as would generally occur to one skilled in the art. Additionally, the diameter of the lighted grip 20 can vary depending on the tool or device in which the lighted grip 20 is attached. The lighted grip 20 can be formed from any material as is known in the art, such as steel, aluminum, or plastic.

Figure 2:
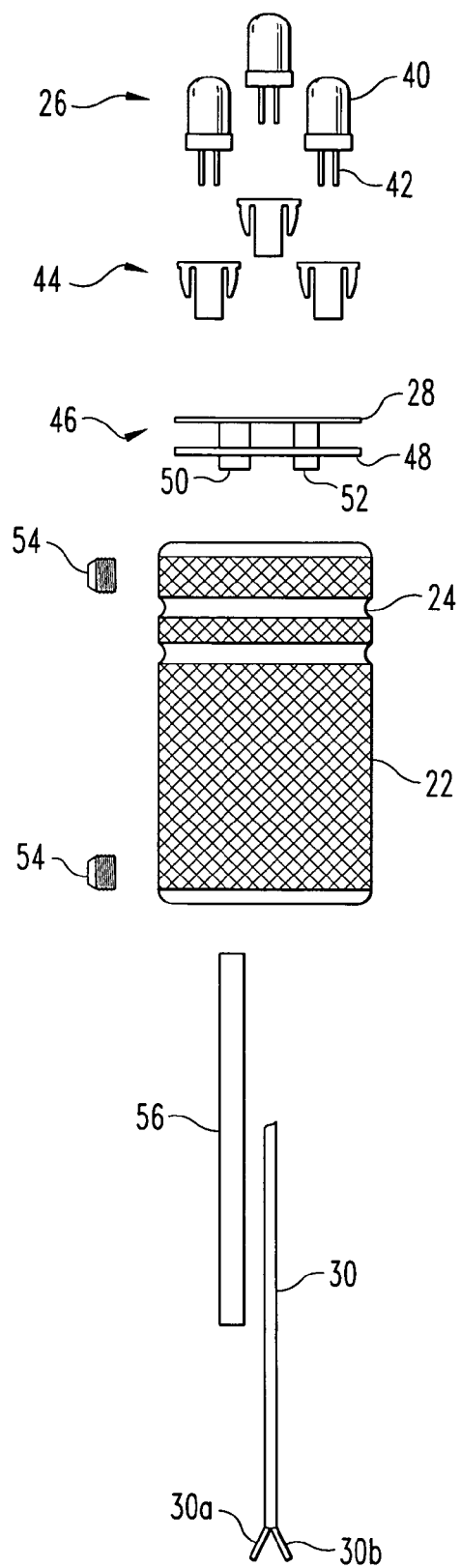
FIG. 2 is an exploded view of a lighted grip assembly.

FIG. 2 is an exploded view illustrating various components of the lighted grip 20. The LEDs 26 include a light 40 and a diode lead 42. In the illustrated embodiment, there are three LEDs 26; however, it should be appreciated that LEDs 26 can number more or less than three. Mounting clips 44 secure the connection of LEDs 26 into a circuit board assembly 46. The circuit board assembly 46 includes the plate 28, as shown in FIG. 1, a circuit board 48, screw receiver 50, and stabilizing spacer 52. The circuit board 48 carries various circuit elements, terminals, resisters, and/or other such components as is known in the art. The wires 30 are operably connected to the circuit board 48, the circuit board 48 being operably connected to the LEDs 26, so as to provide power to the LEDs 26 and light the section of skin 32. The stabilizing spacer 52 is molded directly to the top plate 28 and the circuit board 48, to stabilize the circuit board assembly 46 when in use. Grip tube 22 receives screws 54 to secure the lighted grip 20 to the tattoo machine 34 or other such device. Also illustrated in FIG. 2 is screw 56 and wires 30, including the positive wire 30a and the negative wire 30b. The screw 56 is received in screw receiver 50 to secure the LEDs 26, mounting clips 44, and circuit board assembly 46 within the grip tube 22. Additionally, in one embodiment, the screw 56 has a diameter of one-eighth of an inch. However, it should be understood that the screw 56 can be of a diameter and size as would generally occur to one skilled in the art.

Sterilization of items directly or indirectly involved in the tattooing, medical, and/or dental procedures is an important aspect of the processes. Most often, any items which may come into contact with bodily fluids, bio-contaminants, or other bio-hazardous materials must be disposed of or sterilized after each use. In a preferred embodiment, the grip tube 22 is reusable, and thus removed after each use and sterilized in a chemical or heat based sterilization process, or other such method of sterilization as is known in the art. Additionally, the LEDs 26, mounting clips 44, and circuit board assembly 46, if not disposed of after each use or procedure, may require sterilization. The LEDs 26 are better suited for a chemical based sterilization procedure, as a heat based sterilization procedure may impair the functionality of the LEDs 26. Therefore, it is important to note that the LEDs 26, mounting clips 44, and circuit board assembly 46 are designed to be easily removable from the lighted grip 20 and sterilized in an appropriate manner or disposed of after each use.

Figure 3A:
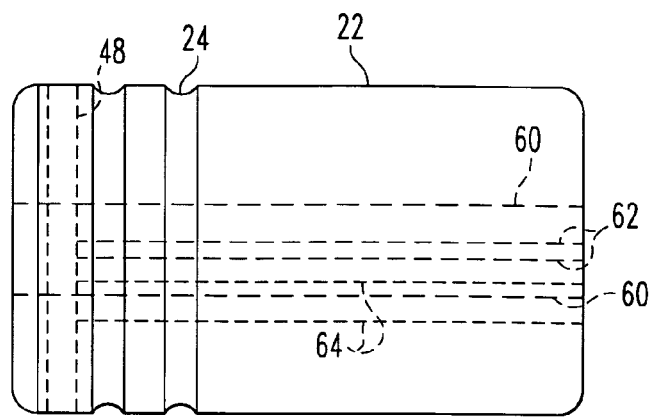
FIG. 3A is a top view of a lighted grip assembly.
Figure 3B:
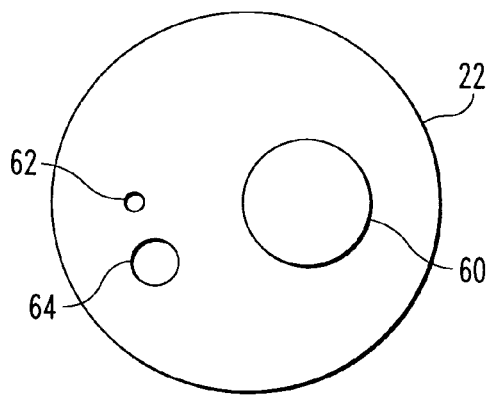
FIG. 3B is a back view of a lighted grip assembly.
Figure 3C:
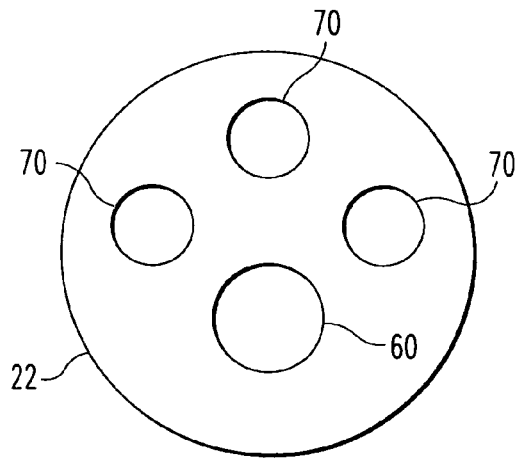
FIG. 3C is a front view of a lighted grip assembly.

FIG. 3A illustrates the grip tube 22 and the various holes are be formed within the grip tube 22 to operate the lighted grip 20. A machine hole 60 provides for insertion of the tattoo machine 34 or other such device. A wire hole 62 provides for insertion of the wires 30 which terminate at the circuit board 48. Further, a screw hole 64 provides for insertion of the screw 56, the screw 56 being received in screw receiver 50. FIG. 3B illustrates the distal end of the grip tube 22, the distal end being the end farthest from the section of skin 32 when the lighted grip 20 is in use. The distal end of the grip tube 22 includes the machine hole 60, the wire hole 62, and the screw hole 64. FIG. 3C illustrates the proximal end of the grip tube 22, the proximal end being the end closest to the section of skin 32 when the lighted grip 20 is in use. The distal end of the grip tube 22 includes the machine hole 60 and holes 70 through which the LEDs 26 extend to light the section of skin 32.

Figure 4A:
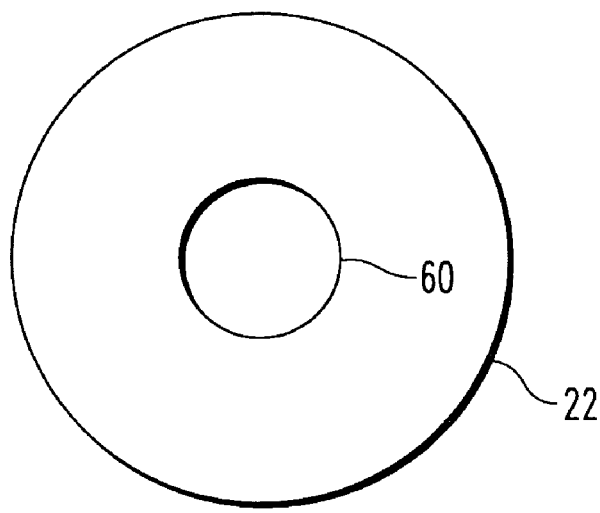
FIG. 4A is a front view of a lighted grip assembly.
Figure 4B:
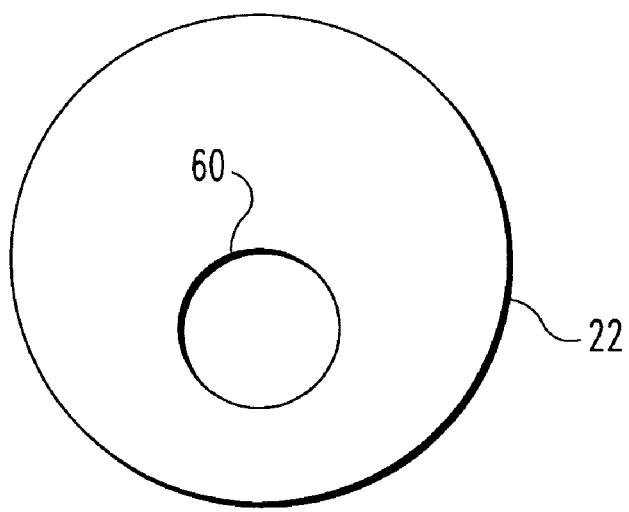
FIG. 4B is a front view of a lighted grip assembly.

FIG. 4A illustrates a preferred embodiment in which the machine hole 60 is centered within the grip tube 22. FIG. 4B illustrates another preferred embodiment in which the machine hole 60 is offset from the center of the grip tube 22.

Figure 5A:
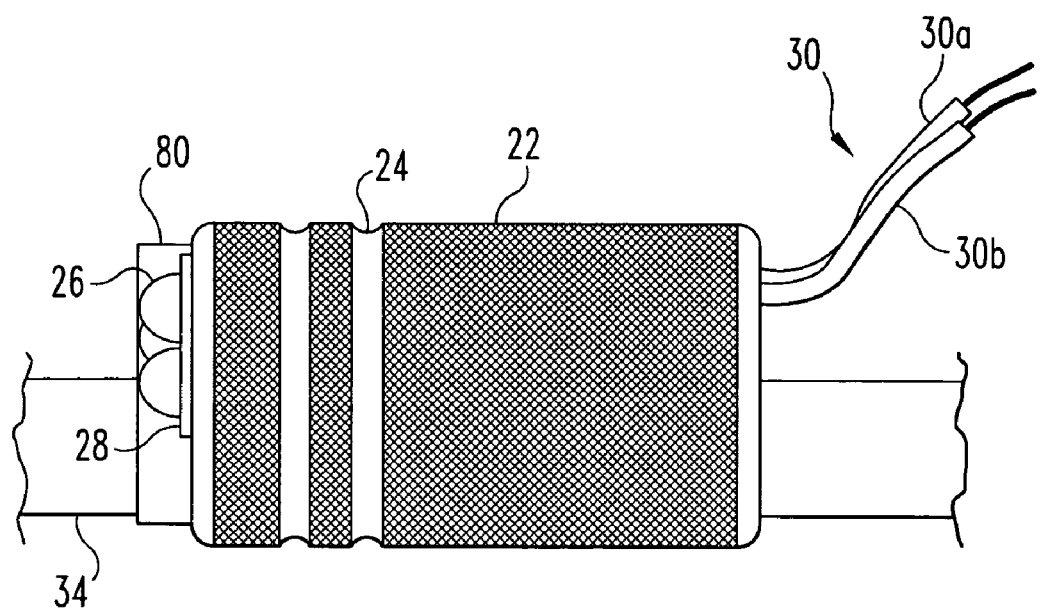
FIG. 5A is a side view of a lighted grip assembly.

FIG. 5A illustrates another preferred embodiment of the present invention incorporating a transparent lens cover 80. Preferably, the lens cover 80 is composed of a transparent material that can be sterilized after each use or disposed of each after each use in an appropriate manner consistent with disposal of bio-hazardous material. The lens cover 80 provides protection to the LEDs 26 from particulate, contaminates, and/or other elements that can contact the LEDs 26, encouraging the reuse of the LEDs 26 through a chemical sterilization process.

Figure 5B:
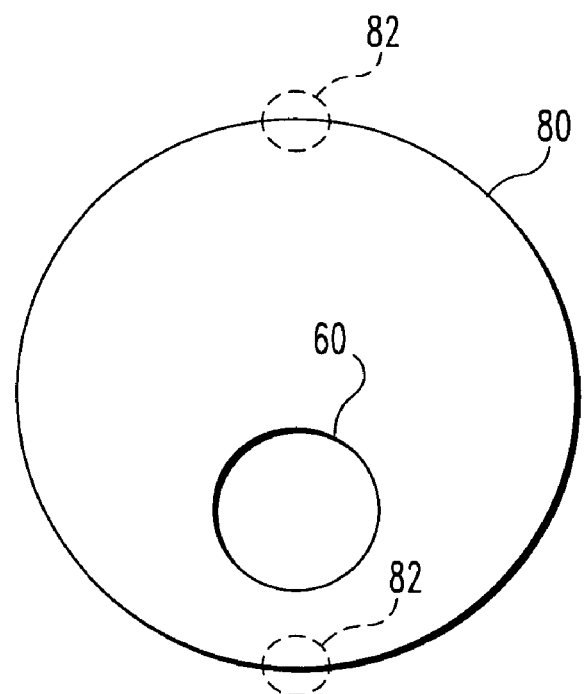
FIG. 5B is a front view of a lighted grip assembly, including a transparent end cap.

FIG. 5B illustrates the front view of the lens cover 80 according to another embodiment of the present invention. The machine hole 60 extends through the lens cover 80 to allow for insertion of the tattoo machine 34 or other similar surgical tool. In one embodiment, the lens cover 80 is connected to the grip tube 22 by screws 82. However, it should be appreciated that the lens cover 80 connects to the proximal end of the grip tube 22 by any appropriate method as would generally occur to one skilled in the art.

Figure 6:
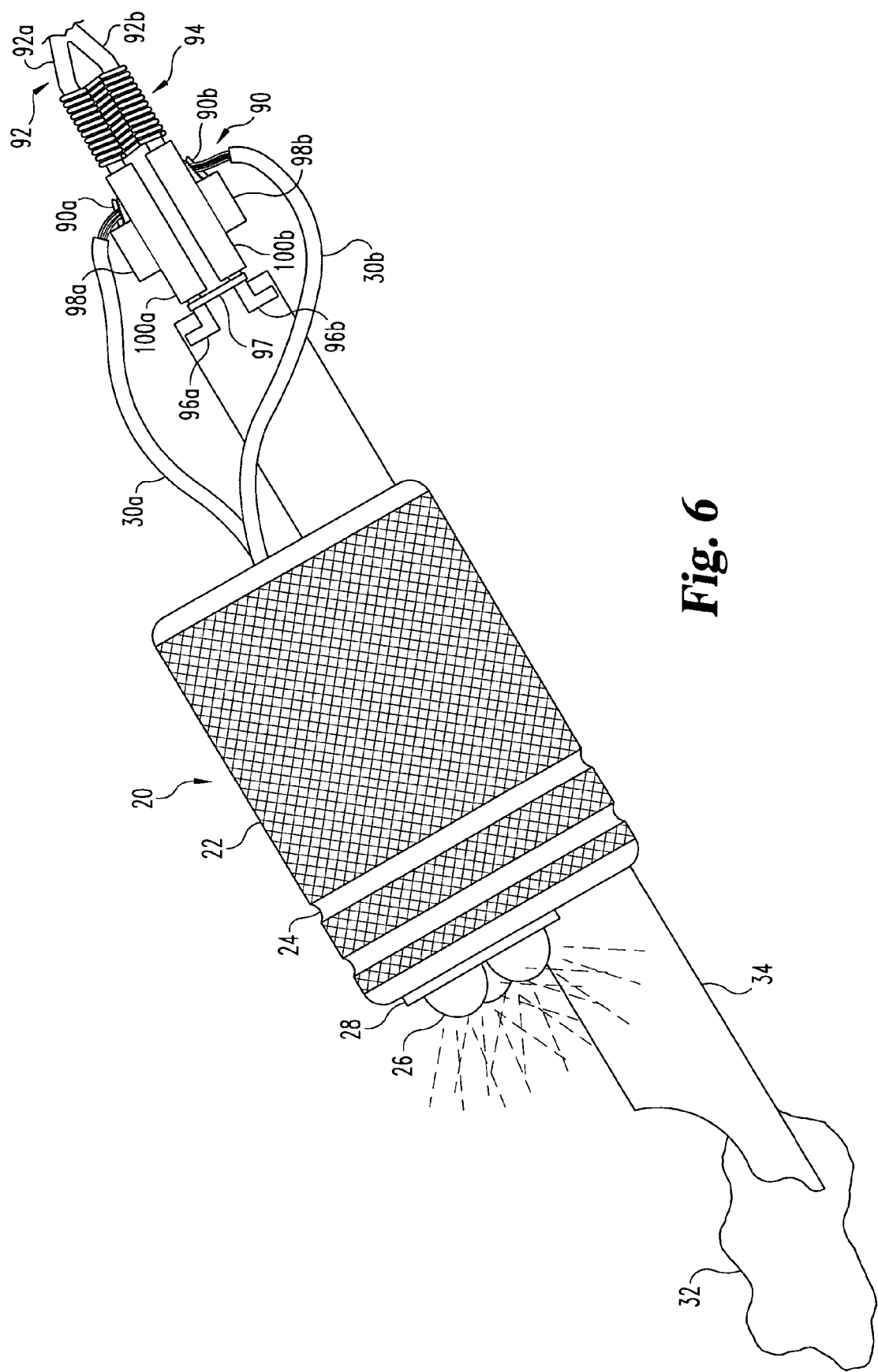
FIG. 6 is a perspective view of a lighted grip assembly utilizing alligator clips.

Another preferred embodiment of the present invention incorporating alligator clips 90 is illustrated in FIG. 6. In the illustrated embodiment, alligator clips 90 transmit power to the lighted grip 20. However, it should be appreciated that the alligator clips 90 can be utilized to provide power to various accessories to a tattoo machine or surgical tool. Alligator clips 90 consist of a positive alligator clip 90a and a negative alligator clip 90b, designed for receipt of the positive power wire 30a and the negative power wire 30b, respectively. The configuration of the wires 30 extending from the distal end of the grip tube 22 to the alligator clips 90 keeps the wires from interfering with the user or operator of the lighted grip 20 and the tattoo machine 34. In the illustrated embodiment, the alligator clips 90 are permanently and conductively connected to a power cord 92. Additionally, the alligator clips 90 are made of an electrically conductive metal and include internal tension springs, as is known in the art, to maintain contact with the wires 30. Power cord 92 connects to a power supply (not shown) at a distal end and connects to the tattoo machine 34 at a proximal end. Electric current flowing from the power supply, through the power cord 92, reaches the alligator clips 90 and travels through the wires 30 to provide power to the lighted grip 20. In one embodiment, the power cord 92 is composed of copper wire.

At the proximal end, power cord 92 separates into a positive cord 92a and a negative cord 92b. Also at the proximal end, the power cord 92 incorporates a tension spring 94, "L" shaped clips 96a and 96b, and a band 97 for connection to the tattoo machine 34. The tension spring 94 is a bias tension spring, encouraging the L clip 96a to extend away from the L clip 96b, and vice versa, enabling the L clips 96a and 96b to stay in contact with the tattoo machine 34. The band 97 assists the tension spring 94 in limiting the distance in which the L clips 96a and 96b extend outward. Additionally, in a preferred embodiment, the alligator clip 90a and the alligator clip 90b contain protective sheaths 98a and 98b, respectively, that include a designation a positive connection point, such as clip 90a, or a negative connection point, such as clip 90b. In a further preferred embodiment, positive cord 92a and negative cord 92b contain protective sheaths 100a and 100b. The protective sheaths 98a, 98b, 100a, and 100b can be composed of a flexible plastic material or other such material as is known in the art. The area of the connection between the power cord 92 and the tattoo machine 34 often rests on the wrist of an operator during use. It is important to note that the alligator clips 90 are lightweight and thus do not add substantial weight to the components resting on the operator's wrist.

Figure 7:
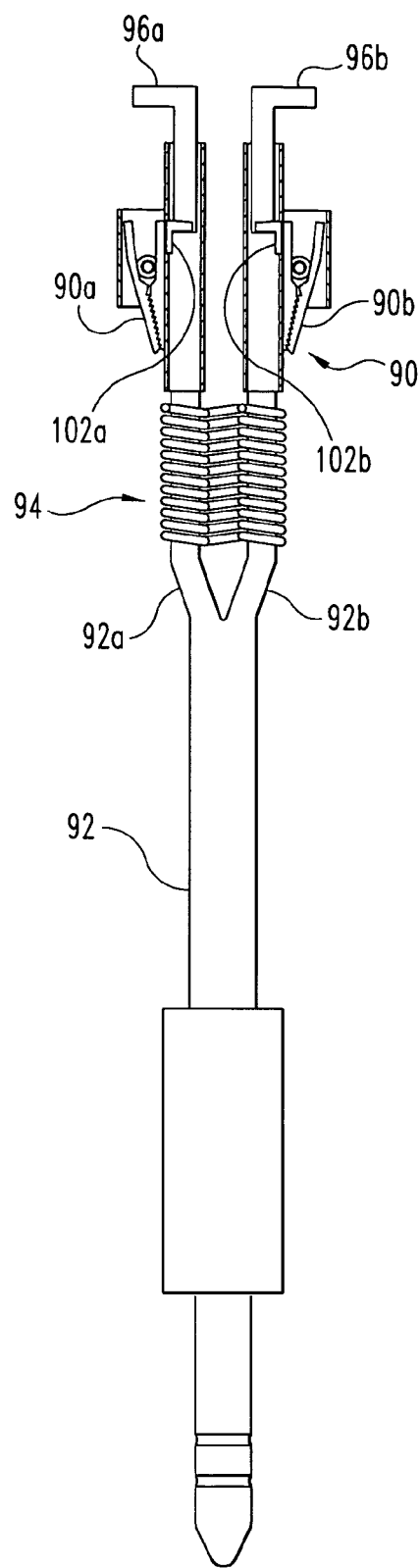
FIG. 7 is a side, partial cross-sectional view of a power cord incorporating alligator clips.

FIG. 7 further illustrates the preferred connection between the power cord 92 and the alligator clips 90. Specifically, the alligator clips 90a and 90b are mounted onto mounting brackets 102a and 102b, respectively, and in conductive connection therewith. Additionally, the mounting brackets 102a and 102b are mounted to the L clips 96a and 96b, respectively, and in conductive connection therewith. Alligator clips 90a and 90b, as well as L clips 96a and 96b, are conductively connected to mounting brackets 102a and 102b in any appropriate manner as is known in the art, such as crimping or soldering. The conductive connections allow the electric current to travel to the lighted grip 20 and thus illuminate the section of skin 32.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A tattoo assembly, comprising:
a tattoo machine for injecting ink into skin;
a grip for attachment to the tattoo machine;
a light assembly disposed partially within the grip, wherein the light assembly includes at least one light emitting diode and a circuit board;
a power supply for powering the tattoo machine and the light assembly;
a power cord for connecting the tattoo machine to the power supply;
a first alligator clip and a second alligator clip, wherein the first alligator and second alligator clip are conductively connected to the power cord for supplying power to the light assembly; and
a first wire and a second wire, wherein the first wire extends from the light assembly to the first alligator clip and the second wire extends from the light assembly to the second alligator clip.

2. The assembly of claim 1, wherein:
the power cord includes a proximal end and a distal end;
the distal end connects to the power supply;
the proximal end connects to the tattoo machine;
the proximal end includes a tension spring, a first connector, and a second connector; and
the first connector and second connector are conductively coupled to the tattoo machine through use of the tension spring.

3. The assembly of claim 2, further comprising:
a first mounting bracket and a second mounting bracket, wherein the first alligator clip is conductively connected to the first mounting piece and the second alligator clip is conductively connected to the second mounting piece, and wherein the first mounting piece is conductively connected to the first connector and the second mounting piece is conductively connected to the second connector.

4. The assembly of claim 3, wherein:
the first alligator clip is a positive power connection and the second alligator clip is a negative power connection;
the first wire is a positive power wire and the second wire is a negative power wire; and
the first wire is conductively connected to the first alligator clip and the second wire is conductively connected to the second alligator clip.

5. The assembly of claim 4, wherein:
the first alligator clip includes a positive power designation and the second alligator clip includes a negative power designation; and
the positive power designation is a red covering, partially encompassing the first alligator clip, and the negative power designation is a black covering, partially encompassing the second alligator clip.

6. The assembly of claim 1, wherein:
the grip includes a proximal end and a distal end;
the distal end is closest to the power cord;
the first wire extends from inside the grip, through the distal end of the grip, to the first alligator clip;
the second wire extends from inside the grip, through the distal end of the grip, to the second alligator clip; and
the at least one light emitting diode is housed partially within the grip and extends out the proximal end of the grip to project light onto a section of skin.

7. The assembly of claim 1, wherein:
the at least one light emitting diode is operably connected to the circuit board; and
the circuit board is operably connected to the first wire and the second wire.

8. The assembly of claim 1, wherein:
the grip has a longitudinal axis and a radial axis; and
the longitudinal axis is perpendicular to the radial axis.

9. The assembly of claim 8, wherein:
the grip includes at least one groove disposed circumferentially about the longitudinal axis.

10. The assembly of claim 8, wherein:
the grip defines an inner hole;
the inner hole runs along the longitudinal axis of the grip; and
the tattoo machine extends through the inner hole of the grip.

11. The assembly of claim 1, wherein:
the at least one light emitting diode has a diameter in the range of 0.1 mm to 5 mm.

12. The assembly of claim 1, further comprising:
at least one mounting clip, wherein the at least one mounting clip is operably connected to the circuit board, and wherein the at least one mounting clip houses the at least one light emitting diode.

13. The assembly of claim 1, further comprising:
at least one first screw to mount the grip to the tattoo machine; and at least one second screw to connect the light assembly to the grip.

14. The assembly of claim 1, frrther comprising:
an end cap surrounding the proximal end of the grip, wherein the end cap covers the at least one light emitting diode.

15. The assembly of claim 14, wherein:
the end cap is transparent.

* * * * *